(12) United States Patent
Akiyama et al.

(10) Patent No.: US 6,368,635 B1
(45) Date of Patent: Apr. 9, 2002

(54) GASTROINTESTINAL MUCOSA-ADHERENT MATRIXES PHARMACEUTICAL PREPARATIONS AND A COATING COMPOSITION

(75) Inventors: Yohko Akiyama, Osaka; Naoki Nagahara, Amagasaki; Shin-ichiro Hirai, Kyoto, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 08/993,314

(22) Filed: Dec. 18, 1997

Related U.S. Application Data

(62) Division of application No. 08/697,166, filed on Aug. 20, 1996, now Pat. No. 5,731,006, which is a division of application No. 08/412,591, filed on Mar. 29, 1995, now Pat. No. 5,576,025, which is a continuation of application No. 08/200,539, filed on Feb. 22, 1994, now abandoned, which is a continuation of application No. 07/870,637, filed on Apr. 20, 1992, now abandoned.

(30) Foreign Application Priority Data

Apr. 19, 1991 (JP) .............................. 3-116745
Aug. 9, 1991 (JP) .............................. 3-225155

(51) Int. Cl.$^7$ ........................... A61K 9/16; A61K 47/34
(52) U.S. Cl. ...................................... 424/501; 424/486
(58) Field of Search ............................. 424/484, 486, 424/501

(56) References Cited

U.S. PATENT DOCUMENTS

| | | | |
|---|---|---|---|
| 3,922,339 A | 11/1975 | Shear | 424/498 |
| 4,173,626 A | 11/1979 | Dempski et al. | 424/499 |
| 4,250,163 A | 2/1981 | Nagai et al. | 424/14 |
| 4,404,183 A | 9/1983 | Kawata et al. | 424/501 |
| 4,439,453 A | 3/1984 | Vogel | 424/498 |
| 4,522,804 A | 6/1985 | Dunn | 424/502 |
| 4,590,068 A | 5/1986 | Berthe et al. | 428/402 |
| 4,664,915 A | 5/1987 | Simonian | 424/692 |
| 4,808,413 A | 2/1989 | Joshi et al. | 424/489 |
| 4,935,245 A | 6/1990 | Horn et al. | 424/502 |
| 4,970,075 A | 11/1990 | Osh Lack | 424/502 |
| 5,026,560 A | 6/1991 | Makino et al. | 424/497 |
| 5,091,184 A | 2/1992 | Khanna | 424/435 |
| 5,102,666 A | 4/1992 | Acharya | 424/501 |
| 5,169,645 A | * 12/1992 | Shukla et al. | |

FOREIGN PATENT DOCUMENTS

| | | |
|---|---|---|
| EP | 0205282 | 12/1986 |
| EP | 0368247 | 5/1990 |
| EP | 0376891 | 7/1990 |
| EP | 0382489 | 8/1990 |
| EP | 0406856 | 1/1991 |
| EP | 0455391 | 11/1991 |
| GB | 2040680 | 9/1980 |
| GB | 2081092 | 2/1982 |
| JP | 55-79323 | 6/1980 |
| JP | 57-21314 | 2/1982 |
| JP | 61-148115 | 7/1986 |
| JP | 63-101332 | 5/1988 |
| JP | 2-193914 | 7/1990 |
| WO | WO89/10117 | 11/1989 |

OTHER PUBLICATIONS

LEhr et al., *Journal of Controlled Release*, vol. 13, No. 1, Jul. 1990, pp. 51–62.
Junginger et al., *Deutsche Apotheker Zeitung*, vol. 130, No. 15, Apr. 12, 1990, pp. 791–801.
Ch'ng et al., *Journal of Pharmaceutical Sciences*, vol. 74, No. 4, Apr. 1985, p. 399.
Longer et al., *Journal of Pharmaceutical Sciences*, vol. 74, No. 4, Apr. 1985, p. 406.

* cited by examiner

*Primary Examiner*—Edward J. Webman
(74) *Attorney, Agent, or Firm*—Wenderoth, Lind & Ponack, L.L.P.

(57) ABSTRACT

A solid matrix composition which is solid at ambient temperature, which comprises a viscogenic agent, such as an acrylic acid polymer, capable of developing viscosity on contact with water, as dispersed at least in the neighborhood of the surface layer of a matrix particle containing a polyglycerol fatty acid ester or a lipid and an active ingredient. The matrix may be such that a matrix particle containing a polyglycerol fatty acid ester or a lipid and an active ingredient has been coated with a coating composition containing at least one viscogenic agent. Such composition can adhere to the digestive tract and remain there for a prolonged period of time, thereby increasing the bioavailability of the active ingredient. Solid preparations, such as fine granules and granules, contain the above matrix composition.

33 Claims, No Drawings

GASTROINTESTINAL MUCOSA-ADHERENT MATRIXES PHARMACEUTICAL PREPARATIONS AND A COATING COMPOSITION

This is a divisional application of now allowed Ser. No. 08/697,166 filed Aug. 20, 1996, now U.S. Pat. No. 5,731,006, which is a divisional application of Ser. No. 08/412,591 filed Mar. 29, 1995, now U.S. Pat. No 5,576,025, which is a continuation application of now abandoned Ser. No. 08/200,539 filed Feb. 22, 1994, which is a continuation application of now abandoned Ser. No. 07/870,637 filed Apr. 20, 1992.

FIELD OF THE INVENTION

The present invention relates to a gastrointestinal mucosa-adherent matrix adapted to stay long in the gastrointestinal tract for sustained drug release, a pharmaceutical preparation based on the matrix, and a coating composition which renders dosage forms adherent to the mucosa.

BACKGROUND OF THE INVENTION

Controlled-release drug delivery systems, particularly sustained-release preparations, are advantageous in that they help to reduce the frequency of administration of a drug without detracting from the effect of medication, prevent any sudden elevation of the blood concentration of the drug to reduce the risk of side effects, and maintain a therapeutically effective blood concentration for an extended period of time. Therefore, much research has been undertaken in the field of controlled release technology from the aspects of active drug, formulation and dosage form. By way of illustration, there are known an encapsulated preparation such that a core containing an active ingredient is covered with a shell, and a matrix type preparation such that an active ingredient has been dispersed in a release-controlling layer. These preparations are generally provided in such dosage forms as tablets, capsules and granules.

Meanwhile, many drug substances are absorbed mostly from the small intestine and, to a lesser extent, from the large intestine. Moreover, in humans, reportedly it takes about 5 to 6 hours for an orally administered drug to reach the large intestine.

However, in oral administration, the residence time of the drug in the digestive canal is of necessity limited even if its release is critically controlled by a sophisticated controlled release system, so that the drug is not efficiently absorbed but is excreted from the body without being fully utilized. Furthermore, in the case of a drug substance which acts directly and locally to produce the expected effect, it is likewise excreted without being utilized if the duration of contact is short. Particularly in cases in which the drug substance is sparingly soluble, its pharmacologic actions cannot be effectively utilized. Therefore, in the conventional drug delivery systems, it is difficult to insure absorption of active ingredients beyond a limited time period.

European Patent Publication No. 0368247A3 discloses a matrix preparation such that a pharmaceutically active ingredient is dispersed in a polyglycerol fatty acid ester-based matrix which is solid at ambient temperature. Moreover, European Patent Publication No. 0406856A2 discloses an FGF protein composition which is a granulated preparation using a polyglycerol fatty acid ester. Furthermore, European Patent Publication No. 0455391 proposes a granulated preparation prepared by thermal fluidization of a particulate composition containing a granular polyglycerol fatty ester having a melting point of 40 to 800° C. and an active ingredient.

However, none of these prior art literature teach or suggest a pharmaceutical preparation having a gastrointestinal mucosa-adherent property.

SUMMARY OF THE INVENTION

It is an object of the present invention to provide a gastrointestinal mucosa-adherent matrix adapted to attach itself to the gastrointestinal mucosa to thereby remain within the gastrointestinal tract for a long period of time and promote absorption of the active ingredient for improved bioavailability.

It is another object of the invention to provide a gastrointestinal mucosa-adherent matrix adapted to attach itself to a specific site within the gastrointestinal tract to thereby allow an active ingredient to act directly on the living body.

It is still another object of the invention to provide a gastrointestinal mucosa-adherent matrix which allows even a sparingly water-soluble active ingredient to be effectively utilized by the body.

A further object of the invention is to provide a pharmaceutical preparation having the above-mentioned beneficial characteristics.

Yet another object of the invention is to provide a coating composition which renders a drug substance or dosage form adherent to the gastrointestinal mucosa.

The inventors of the present invention found that the duration of action of various active ingredients can be prolonged by incorporating a certain substance having the property to become viscous on contact with water (hereinafter referred to as "viscogenic agent") in a pharmaceutical composition or coating a pharmaceutical composition with such a viscogenic agent. The present invention has been completed based on these findings.

Thus, the present invention provides a gastrointestinal mucosa-adherent matrix which is solid at ambient temperature, and which contains a viscogenic agent as dispersed at least in the neighborhood of the surface layer of a matrix particle containing a polyglycerol fatty acid ester and/or a lipid and an active ingredient.

The above gastrointestinal mucosa-adherent matrix which is solid at ambient temperature includes a matrix in which each matrix particle containing a polyglycerol fatty acid ester and/or a lipid and an active ingredient has a coating layer comprising or containing the viscogenic agent.

The present invention further provides a solid pharmaceutical preparation based on the matrix, which may be in the form of fine granules or granules.

The present invention further provides a coating composition comprising at least the viscogenic agent. The coating composition may further contain at least one member selected from the group consisting of polyglycerol fatty acid esters, lipids, enteric polymers and water-insoluble polymers.

As used throughout this specification, the term "gastrointestinal mucosa-adherent" refers to any and all cases in which the property of adhering to the gastrointestinal mucosa is exhibited or imparted by the viscogenic agent, including cases in which the matrix additionally has an enteric or gastric coating layer which does not contain the viscogenic agent. The term "the neighborhood of the surface layer" means not only the surface of the matrix particle but also the region adjoining to the surface, including a coating layer such as the one mentioned above.

The term "coating" is used herein to mean not only a process in which the whole surface of a matrix particle is covered with a coating composition containing the viscogenic agent but also a process in which the surface of the matrix particle is partially covered with such a coating composition.

It should also be understood that where the matrix and/or the polyglycerol fatty acid ester or the like is a mixture, the composition does not show a distinct melting point but softens at a specific temperature. The term "melting point" as used in this specification includes the softening point displayed by such a mixture.

DETAILED DESCRIPTION OF THE INVENTION

The viscogenic agent used in the present invention may be any substance that develops a sufficient degree of viscosity in the presence of water to adhere to the gastrointestinal mucosa and is pharmaceutically acceptable. Preferred species of the viscogenic agent swell or gain in viscosity to a remarkable extent on contact with water. As examples of such viscogenic agent, there may be mentioned polymers containing carboxyl groups or salts thereof, cellulose ethers, polyethylene glycols having molecular weights not less than 200,000, and naturally-occurring mucous substances. The preferable viscogenic agents are those having a viscosity in the range of 3 to 50,000 cps, preferably 10 to 30,000 cps, and more preferably 15 to 30,000 cps as a 2 percent by weight aqueous solution thereof at 20° C. When a polymer becomes viscous by neutralization, the viscosity of a 0.2 percent by weight aqueous solution of the viscogenic agent is, for example, in the range of 100 to 500,000 cps, preferably 100 to 200,000 cps, and more preferably 1,500 to 100,000 cps at 20° C. In the present invention, at least one of such viscogenic agents is employed, and needless to say, two or more species of said viscogenic agents may be employed in combination.

The polymers containing carboxyl groups or salts thereof include, for example, acrylic acid polymers obtainable by polymerization of a monomer containing acrylic acid and salts thereof as a monomer component. The salts may be the corresponding salts of monovalent metals such as sodium, potassium, and the like and of divalent metals such as magnesium, calcium, and the like. Such acrylic acid polymers and salts preferably contain 58.0 to 63.0 percent by weight of carboxyl groups and have molecular weights of 200,000 to 6,000,000 and preferably 1,000,000 to 5,000,000. The preferred acrylic polymers include an acrylic acid homopolymer or a salt thereof. Such polymers are described as carboxyvinyl polymers in the Formulary on Non-official Drugs (October, 1986). As specific examples of polymers in this category, there may be mentioned carbomers [Trade name: Carbopol (hereinafter referred to as Carbopol), The B. F. Goodrich Company] 910, 934, 934P, 940, 941, 1342 (NF XVII) , etc., HIVISWAKO 103, 104, 105 (Trade name of Wako Pure Chemical Industries, Japan), NOVEON AA1 (Trade name of The B. F. Goodrich Company), Calcium Polycarbophil (USP XXII) and so on.

The cellulose ethers mentioned above include, for example, carboxymethylcellulose sodium (sometimes referred to briefly as CMC-sodium) (The Pharmacopoeia of Japan (hereinafter referred to as J.P.) XI ], hydroxypropylmethylcellulose 2208, 2906 [e.g. HPMC-65SH50, HPMC-65SH4000 (Trade name of Shin-Etsu Chemical Co., Ltd., Jaan)], 2910 [e.g. TC-5 (Trade name of Shin-Etsu Chemical Co., Ltd., Japan)] (J.P. X), methylcellulose, crystalline cellulose-carboxymethylcellulose sodium (e.g. Avicel RC) (the Formulary of Non-official Drugs) and so on.

The naturally-occurring mucous substances include, for example, mucin, agar, gelatin, pectin, carrageenan, sodium alginate, locust bean gum, xanthan gum, tragacanth gum, arabic gum, chitosan, pullulan, waxy starch and so on.

Preferred viscogenic agents contain at least one of the acrylic acid polymers and salts thereof. Particularly preferred viscogenic agents are acrylic acid polymers and salts thereof.

The polyglycerol fatty acid esters are esters of polyglycerols with fatty acids and may be monoesters, diesters or polyesters. The polyglycerol fatty acid esters show no crystal polymorphism and are characterized in that they hardly interact with pharmacologically active ingredients. Therefore, the ingredient in the presence of a polyglycerol fatty acid ester is deactivated only slightly and remains stable for a long time.

Polyglycerol is a "polyhydric alcohol containing each molecule n (cyclic form) to n+2 (straight or branched form) hydroxyl groups and n−1 (straight or branched form) to n (cyclic form) ether bonds" ["Polyglycerin Ester", edited by Sakamoto Yakuhin Kogyo Co., Ltd., Japan, published May 2, 1986, page 12] and the compound of the following formula (I), for instance, can be employed.

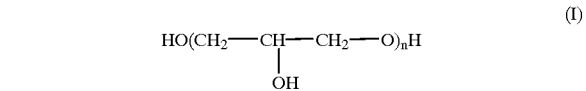

(I)

wherein n represents the degree of polymerization which is an integer of not less than 2.

In the above formula, n is generally 2 to 50 preferably 2 to 20, and more preferably 2 to 10. The polyglycerols need not be straight-chain but may be branched.

Typical examples of such polyglycerol are diglycerol, triglycerol, tetraglycerol, pentaglycerol, hexaglycerol, heptaglycerol, octaglycerol, nonaglycerol, decaglycerol, pentadecaglycerol, eicosaglycerol, triacontaglycerol and so on. Of these species of polyglycerol, tetraglycerol, hexaglycerol and decaglycerol are used most frequently.

The fatty acids include, for example, saturated or unsaturated higher fatty acids containing 8 to 40 carbon atoms, preferably 12 to 22 carbon atoms. Thus, for example, palmitic acid, stearic acid, oleic acid, linoleic acid, linolenic acid, myristic acid, lauric acid, ricinoleic acid, caprylic acid, capric acid, behenic acid, etc. may be mentioned. Among these fatty acids, for example, stearic acid, oleic acid, lauric acid, ricinoleic acid and behenic acid are preferred.

As specific examples of such polyglycerol fatty acid ester, there may be mentioned behenyl hexa(tetra)glyceride, caprylyl mono(deca)glyceride, caprylyl di(tri)glyceride, capryl di(tri)glyceride, lauryl mono(tetra)glyceride, lauryl mono(hexa)glyceride, lauryl mono(deca)glyceride, oleyl mono(tetra)glyceride, oleyl mono(hexa)glyceride, oleyl mono(deca)glyceride, oleyl di(tri)glyceride, oleyl di(tetra) glyceride, oleyl sesqui(deca)glyceride, oleyl penta(tetra) glyceride, oleyl penta(hexa)glyceride, oleyl deca(deca) glyceride, linolyl mono(hepta)glyceride, linolyl di(tri) glyceride, linolyl di(tetra)glyceride, linolyl di(hexa) glyceride, stearyl mono(di)glyceride, stearyl mono(tetra) glyceride, stearyl mono(hexa)glyceride, stearyl mono(deca) qlyceride, stearyl tri(tieitra)glyceride, stearyl tri(hexa) glyceride, stearyl sesqui(hexa)glyceride, stearyl penta(tetra) glyceride, stearyl penta(hexa)glyceride, stearyl deca(deca) glyceride, palmityl mono(tetra)glyceride, palmityl mono (hexa)glyceride, palmityl mono(deca)glyceride, palmityl tri (tetra)glyceride, palmityl tri(hexa)glyceride, palmityl sesqui (hexa)glyceride, palmityl penta(tetra)glyceride, palmityl penta(hexa)glyceride, palmityl deca(deca)glyceride and so on.

Preferred polyglycerol fatty acid esters include, for example, behenyl hexa(tetra)glyceride (e.g. Riken Vitamin Co., Ltd., Japan; Poem J-46B, etc.), stearyl penta(tetra) glyceride (e.g. Sakamoto Yakuhin Kogyo Co., Ltd., Japan: PS-310), stearyl mono(tetra)glyceride (e.g. Sakamoto Yakuhin Kogyo Co., Ltd., Japan; MS-310), stearyl penta(hexa) glyceride (e.g. Sakamoto Yakuhin Kogyo Co., Ltd., Japan; PS-500), stearyl sesqui(hexa)glyceride (e.g. Sakamoto Yakuhin Kogyo Co., Ltd., Japan; SS-500) and stearyl mono (deca)glyceride, as well as mixtures thereof.

These polyglycerol fatty acid esters may be used either singly or in combination.

The molecular weight of the polyglycerol fatty acid ester is generally about 200 to 5000, preferably about 300 to 2000 and more preferably about 500 to 2000. The HLB (hydrophile-lipophile balance) number of the polyglycerol fatty acid esters is generally 1 to 22, preferably 1 to 15 and more preferably 2 to 9. The HLB number may be adjusted by using two or more polyglycerol fatty acid esters having different HLB numbers in combination. By varying the HLB number of polyglycerol fatty acid esters, the release and dissolution rates of the active ingredient can be controlled as desired.

While polyglycerol fatty acid esters can be selectively used according to the active ingredient, viscogenic agent and matrix form chosen, those which are solid at ambient temperature (about 15° C.) are employed. The melting point of the polyglycerol fatty acid ester may for example be about 15 to 80° C., preferably about 30 to 75° C. and more preferably about 45 to 75° C.

When two or more polyglycerol fatty acid esters are used as a mixture, one or more of the esters may be liquid provided that the matrix is solid at ambient temperature.

The lipid as a constituent of the matrix is one having a melting point of 40 to 120° C., preferably 40 to 90° C.

Typical examples of the lipid include, for example, saturated fatty acids containing 14 to 22 carbon atoms (e.g. myristic acid, palmitic acid, stearic acid, behenic acid, and the like) and salts thereof (e.g. the corresponding sodium and potassium salts), higher alcohols containing 16 to 22 carbon atoms (e.g. cetyl alcohol, stearyl alcohol, and the like), glycerol fatty acid esters such as monoglycerides, diglycerides and triglycerides of said fatty acids (e.g. 1-monostearin, 1-monopalmitin, and the like), oils (e.g. castor oil, cottonseed oil, soybean oil, rapeseed oil, beef tallow and other hardened oils), waxes (e.g. beeswax, carnauba wax, sperm wax, and the like), hydrocarbons (e.g. paraffin, microcrystalline wax, and the like), phospholipids (e.g. hydrogenated lecithin and the like) and so on. Preferred, among these lipids, are hydrogenated cottonseed oil, hydrogenated castor oil, hydrogenated soybean oil, carnauba wax, stearic acid, stearyl alcohol and microcrystalline wax.

There is no particular limitation on the type of active ingredient. The active ingredient in the present invention includes not only medicaments for human beings but also veterinary drugs. Thus, for example, central nervous system drugs such as antipyretic-analgesic-antiinflammatory agents, hypnotics and sedatives, antlepileptics, antivertigo agents, psychotropic agents, and the like; peripheral nervous system drugs such as skeletal muscle relaxants, autonomic drugs, antispasmodics, and the like; cardiovascular drugs such as cardiotonics, antiarrhythmic agents, diuretics, antihypertensive agents, vasodilators, vasoconstrictors, and the like; respiratory organ drugs such as bronchodilators, antitussives, and the like; digestive organ drugs such as antipeptic ulcer agents, digestants, intestinal function-controlling agents antacids, and the like; hormones; antihistaminics; metabolic drugs such as vitamins; antiulcer drugs; antibiotics; chemotherapeutic agents; and the like may be mentioned.

Since the matrix composition of the present invention adheres to the gastrointestinal mucosa, a sparingly water-soluble active ingredient can be used effectively.

Among specific examples of the active ingredient are indomethacin, salicylic acid, trepibutone, amoxanox, aspirin, valproic acid, ketoprofen, ibuprofen, probenecid, 3,4-dihydro-2,8-diisopropyl-3-thioxo-2H-1,4-benzoxazine-4-acetic acid (hereinafter, AD-5467), isosorbide dinitrate, vinpocetine, estazoram, acetazolamide, papaverine, tolbutamide, acetohexamide, verapamil, quinidine, morphine, buprenorphine hydrochloride, dihydrocodeine phosphate, ephedrine, scopolamine, chlorpromazine, manidipine hydrochloride, phenylpropanolamine hydrochloride, chlorpheniramine maleate, phenylephrine hydrochloride, procainamide hydrochloride, sulfanylamide, molsidomine, sulfadiazine, diazepam, quinidine, N-ethyl-N-demethyl-8,9-anhydroerythromycin A 6,9-hemiketal, epinephrine, reserpine, acetaminophen, theophylline, caffeine, cefalexin, ampicillin, sulfisoxazole, delapril hydrochloride, ipriflavone, 2,2'-[(2-aminoethyl)imino]di-ethanol bis (butylcarbamate) dihydrochloride, cefotiam hexetil hydrochloride, cyclandelate, idebenone [namely, 2-(10-hydroxydecyl)-2,3-dimethoxy-5-methyl-1,4-benzoquinone], propranolol, haloperidol, chlorothiazide, hydrochlorothiazide, sucralfate, vitamins such as riboflavin, ascorbic acid, and the like, minerals, amino acids and so on.

Preferred examples of the active ingredient used in this invention include antiulcer agents and therapeutic agents for gastritis. Typical examples of such antiulcer agents include 2-[(2-pyridyl)methylthio] benzimidazole and its derivatives (there hereinafter may be referred to briefly as benzimidazole compounds) and salts thereof. Among these benzimidazole compounds are the compounds described in Japanese Patent Publication No. 44473/1990 corresponding to U.S. Pat. No. 4,628,098, Japanese Patent Publication No. 38247/1991, and Japanese Patent laid open No. 173817/1991 corresponding to U.S. Pat. No. 5,013,743. To be specific, the compounds of the following formula (II) and physiologically acceptable salts thereof are particularly preferred.

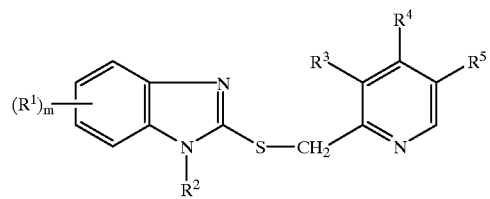

(II)

wherein $R^1$ means hydrogen, an alkyl, a halogen, cyano, carboxy, an alkoxycarbonyl, an alkoxycarbonylalkyl, carbamoyl, a carbamoyalkyl, hydroxy, an alkoxy, a hydroxyalkyl, trifluoromethyl, an acyl, carbamoyloxy, nitro, an acyloxy, an aryl, an aryloxy, an alkylthio or a alkylsufinyl; $R^2$ means hydrogen, an alkyl, acyl, an alkoxycarbonyl, carbamoyl, an alkylcarbamoyl, a dialkylcarbamoyl, an alkylcarbonylmethyl, an alkoxycarbonylmethyl or an alkylsulfonyl; $R^3$ and $R^5$ may be the same or different and each means hydrogen, an alkyl, an alkoxy or an alkoxyalkoxy; $R^4$ means hydrogen, an alkyl, an alkoxy which may be fluorinated, an alkoxyalkoxy, an alkenyloxy which may be fluorinated or an alkynyloxy which may be fluorinated and m means an integer of 0 to 4.

The compound of the formula (II) can be produced by the processes described in the above patent literature or any process analogous thereto.

The substituents on the compound of the formula (II) are now briefly described.

Referring to $R^1$ in the above formula, said alkyl includes an alkyl group of 1 to 7 carbon atoms; the alkoxy of said alkoxycarbonyl includes an alkoxy group of 1 to 4 carbon atoms; the alkoxy of said carbomoylalkyl includes an alkoxy group of 1 to 4 carbon atoms and the alkyl thereof includes an alkyl group of 1 to 4 carbon atoms; the alkyl of said carbomoylalkyl includes an alkyl group of 1 to 4 carbon atoms; said alkoxy includes an alkoxy group of 1 to 5 carbon atoms; the alkyl of said hydroxyalkyl includes an alkyl group of 1 to 7 carbon atoms; said acyl includes an acyl group of 1 to 4 carbon atoms; the acyl of said acyloxy includes an acyl group of 1 to 4 carbon atoms; said aryl includes phenyl; the aryl of said aryloxy includes phenyl; the alkyl of said alkylthio includes an alkyl group of 1 to 6 carbon atoms; and the alkyl of said alkylsulfinyl includes an alkyl group of 1 to 6 carbon atoms.

As represented by $R^2$, said alkyl includes an alkyl group of 1 to 5 carbon atoms; said acyl includes an acyl group of 1 to 4 carbon atoms; the alkoxy of said alkoxycarbonyl includes an alkoxy group of 1 to 4 carbon atoms; the alkyl of said alkylcarbamoyl includes an alkyl group of 1 to 4 carbon atoms; the alkyl of said dialkylcarbamoyl includes an alkyl group of 1 to 4 carbon atoms; the alkyl of said alkylcarbonylmethyl includes an alkyl group of 1 to 4 carbon atoms; the alkoxy of said alkoxycarbonylmethyl includes an alkoxy group of 1 to 4 carbon atoms; and the alkyl of said alkylsulfonyl includes an alkyl group of 1 to 4 carbons.

The alkyl group for $R^3$, $R^4$ and $R^5$ includes an alkyl group of 1 to 4 carbon atoms; the alkoxy includes an alkoxy group of 1 to 8 carbon atoms; and the alkoxy of said alkoxyalkoxy includes an alkoxy group of 1 to 4 carbon atoms.

Referring to $R^4$, the alkoxy of said alkoxy which may be fluorinated includes an alkoxy group of 1 to 8 carbon atoms, the alkenyl of said alkenyloxy which may be fluorinated includes an alkenyl group of 2 to 6 carbon atoms; and the alkynyl of said alkynyloxy which may be fluorinated includes an alkynyl group of 2 to 6 carbon atoms. When the alkoxy, alkenyl or alkynyl group includes fluorinated, the preferred number of substitutions is 1 to 9.

The physiologically acceptable salt of the compound (II) include the corresponding hydrochloride, hydrobromide, hydroiodide, phosphate, nitrate, sulfate, acetate, citrate and so on. These salts can be prepared from the compound of formula (II) by a routine procedure.

The preferred substituents on the compound of the formula (II) are as follows. $R^1$ is hydrogen atom, fluorine atom, methoxy group or trifluoromethyl group and m=1. The substituent $R^2$ is hydrogen atom, $R^3$ is hydrogen atom or methyl group, $R^4$ is a $C_{1-4}$ alkoxy group, a 2-propenyloxy group or an allyl group, which may be fluorinated, $R^5$ is hydrogen atom or methyl group. The preferred position of substitution for $R^1$ is position-4 or position-5 and preferably position-5.

Among compounds of the formula (II), the compounds in which $R^1=R^2=R^5=H$ and $R^3=H$ or $CH_3$ are preferred. Particularly preferred are compounds in which $R^4$ is a fluorinated $C_{1-4}$ alkoxy group. The compounds in which $R^1=R^2=R^5=H$ and $R^3=CH_3$ having the fluorinated $C_{1-4}$ alkoxy group as $R^4$ include, among others, a compound having a 2,2,2-trifluoroethoxy as $R^4$ (hereinafter the compound may be referred to briefly as AG 1777), a compound having a 2,2,3,3-tetrafluoropropoxy as $R^4$ (hereinafter the compound may be referred to briefly as AG 1789), a compound having a 2,2,3,3,3-pentafluoropropoxy as $R^4$ (hereinafter the compound may be referred to briefly as AG1776), a compound having a 2,2,3,3,4,4-hexafluorobutoxy as $R^4$, a compound having a 2,2,3,3,4,4,4-heptafluorobutoxy as $R^4$, and so on.

The benzimidazole compound of the formula (II), inclusive of a pharmacologically acceptable salt thereof, is a therapeutic drug for treating peptic ulcers which has gastric acid antisecretory activity as a main pharmacological action, and gastric mucosa-protecting activity as well. By using the benzimidazole compound or salt in the matrix or solid preparation of the present invention, there can be obtained a more effective therapeutic regimen for treating peptic ulcer.

The active ingredient may be a peptide or a protein. Examples of such a peptide and protein include physiologically active peptides and hormones such as insulin, vasopressin, interferons, IL-2, urokinase, serratiopeptidase, superoxide dismutase (SOD), thyrotropin releasing hormone (TRH), luteinizing hormone releasing hormone (LH-RH), corticotropin releasing hormone (CRF), growth hormone releasing hormone (GHRH), somatostatin, oxytosin, growth hormone, and the like; growth factors such as epidermal growth factor (EGF), nerve growth factor (NGF), insulin-like growth factor (IGF), fibroblast growth factor (FGF) (e.g. aFGF, bFGF, etc.), erythropoietin (EPO); calcitonin, colony stimulating factor (CSF) and so on. bFGF includes rhbFGF muteins, such as CS23 (hereinafter referred to as TGP580; European Patent Publication No. 281822).

Due to their inherent properties, these active ingredients may vary in solubility and the site of absorption within the gastrointestinal tract. Generally speaking, the solubility of basic drugs is high on the acidic side and low on the alkaline side. Therefore, the rate of release of a basic active ingredient in a matrix or preparation is fast in the stomach where the ingredient passes first and the environment is acidic, while it is slow in the intestine where the environment is neutral to weakly alkaline. Conversely the solubility of an acidic drug is high on the alkaline side but low on the acidic side. Therefore, the rate of release of an acidic active ingredient in a matrix or preparation is fast in the intestine where neutral to weakly alkaline conditions prevail and slow in the stomach through which it passes in the first place.

Therefore, in order that an active ingredient may be released at a constant rate in both the stomach and intestine, irrespective of environmental pH, the matrix containing a polyglycerol fatty acid ester or a lipid and being solid at ambient temperature may contain a water-insoluble or sparingly water-soluble solid base together with an acidic active ingredient or an enteric polymer together with a basic active ingredient.

The acidic active ingredient includes various substances whose aqueous solutions, not in the form of salts, are acidic (e.g. pH 1.5 to 7.0, preferably 2.0 to 6.8). Among such acidic active ingredients are, for example, indomethacin, salicylic acid, AD-5467, trepibutone, amoxanox, aspirin, valproic acid, ketoprofen, ibuprofen, ascorbic acid, probenecid and so on. Among these acidic drugs, AD-5467, trepibutone and indomethacin are frequently used.

The solubility of the solid base in water may, for example, be not more than 0.1 g/ml, preferably not more than 0.001 g/ml, at 37° C. Solid bases of low solubility provide satisfactory results. As such solid bases, there may be mentioned the oxides, hydroxides, inorganic acid salts or organic acid salts of metals of Group I, II or III of Periodic Table of the Elements, such as magnesium oxide, magnesium hydroxide, magnesium silicate, magnesium carbonate, aluminum silicate, aluminum hydroxide, silicic acid (Syloid, Aerosil), magnesium metasilicate aluminate (Neusilin), magnesium stearate, calcium stearate, aluminum stearate, sodium stearate and so on. These solid bases may be used singly or in combination.

The particle size of such solid base is generally not more than about 50 μm and preferably about 0.05 to 20 μm. The proportion of the solid base to the total preparation is generally about 1 to 80 percent by weight, preferably about 1 to 50 percent by weight and more preferably about 10 to 30 percent by weight.

The basic active ingredient includes various components whose aqueous solutions, not in the form of salts but in free forms, are basic (for example pH 7.0 to 13.0, preferably pH 7.0 to 10.5). As such basic active ingredients, there may be mentioned vinpocetine, estazolam, acetazolamide, papaverine, tolbutamide, acetohexamide, verapamil, quinidine, morphine, ephedrine, scopolamine, chlorpromazine, manidipine and so on. Among these basic drugs, vinpocetine and acetazolamide are frequently employed.

The enteric polymer is a polymer which dissolves little in the stomach but dissolves in the intestine. Such enteric polymer is preferably an acidic polymer having a molecular weight of about 30,000 to 500,000, preferably about 70,000 to 400,000. As examples of such enteric polymer, there may be mentioned hydroxypropylmethylcellulose phthalate, cellulose acetate phthalate, carboxymethylethylcellulose (CMEC AQ, Trade name of Kohjin Co., Ltd., Japan), methacrylic acidmethyl methacrylate copolymers (Eudragit L100-55, L100and S100, Trade name of Röhm Pharma GmbH, Germany) and so on. These enteric polymers are used singly or in combination. Among these enteric polymers, Eudragit L100-55 is one of the polymers which can be frequently employed.

The enteric polymer is preferably used in finely divided form. The particle size of such enteric polymer is generally not more than about 50 μm and preferably about 0.05 to 10 μm. The content of such enteric polymer based on the total composition is generally about 1 to 80 percent by weight, preferably about 1 to 50 percent by weight, and more preferably about 10 to 30 percent by weight.

The content of the active ingredient to, the whole matrix composition is about 0.0001 to 95 percent by weight and preferably about 0.1 to 90 percent by weight.

The matrix according to the present invention may be classified into (A) a matrix composition such that the viscogenic agent has been dispersed at least in the neighborhood of the surface layer of a matrix particle containing the active ingredient and the polyglycerol fatty acid ester, (B) a matrix composition such that the viscogenic agent has been dispersed in the neighborhood of the surface layer of a matrix particle containing the active ingredient and the lipid, and (C) a matrix composition such that the matrix particle has been coated with a coating composition comprising or containing the viscogenic agent.

The proportion of the polyglycerol fatty acid ester and/or lipid to be incorporated in each matrix particle is about 0.001 to 10,000 parts by weight and preferably about 0.001 to 50 parts by weight relative to a part by weight of the active ingredient.

The matrix particles of matrixes (A) and (C) each containing the polyglycerol fatty acid ester may give still more beneficial effects when a lipid is further incorporated. The lipid for this purpose is a pharmaceutically acceptable water-insoluble substance which is able to control the rate of dissolution of the active ingredient. Among such lipids are the compounds mentioned hereinbefore.

When used in combination with the polyglycerol fatty acid ester, the lipid can be used in a proportion which does not detract from the adhesiveness of the matrix to the gastrointestinal mucosa. Usually, the lipid is used in a proportion of about 0.01 to 100 parts by weight and preferably about 1 to 20 parts by weight relative to a part by weight of the active ingredient.

Unless contrary to the objects of the invention, various additives which are commonly used in the manufacture of solid pharmaceutical preparations, particularly fine granules or granules, may be added to the particles of matrixes (A), (B) and (C). The additives mentioned just above include various excipients such as lactose, corn starch, talc, crystalline cellulose (Avicel and the like), powder sugar, magnesium stearate, mannitol, light silicic anhydride, magnesium carbonate, calcium carbonate, L-cysteine, and the like; binders such as starch, cane sugar, gelatin, powdered gum arabic, methylcellulose, carboxymethylcellulose, carboxymethylcellulose sodium, hydroxypropylcellulose, hydroxypropylmethylcellulose, polyvinylpyrrolidone, pullulan, dextrin, and the like; disintegrators such as carboxymethylcellulose calcium, low-substituted hydroxypropylcellulose, croscarmellose sodium, and the like; surfactants including anionic surfactants such as sodium alkylsulfates and the like and nonionic surfactants such as polyoxyethylene-sorbitan fatty acid esters, polyocyethylene-fatty acid esters and polyoxyethylene-castor oil derivatives, and the like; gastric antacids and mucosa-protecting agents such as magnesium hydroxide, magnesium oxide, aluminum hydroxide, aluminum sulfate, magnesium metasilicate aluminate, magnesium silicate aluminate, sucralfate, and the like; colorants; corrigents; adsorbents; preservatives; wetting agents; antistatic agents; disintegration retarders; and so on. The amounts of these additives can be selected as desired within the range not adversely affecting the adhesion of the final preparation to the mucosa.

The gastrointestinal mucosa-adherent matrixes (A), (B) and (C) according to the invention are solid at ambient temperature. The preferred melting point of these matrixes may for example be about 30 to 120° C. and preferably about 40 to 120° C.

Referring to the matrixes (A) and (B), the viscogenic agent may be dispersed throughout each matrix particle containing the polyglycerol fatty acid ester and/or lipid and the active ingredient or dispersed in a coating film covering the matrix particle. The viscogenic agent in the matrix becomes viscous on contact with water and probably because it bleeds out onto the surface of the matrix particle, the matrix is rendered adherent to the gastrointestinal mucosa. Therefore, the matrix of the invention is retained in the gastrointestinal tract for a long time during which the active ingredient is gradually dissolved within the gastrointestinal tract and absorbed. Furthermore, this matrix adheres efficiently to a specific site of the gastrointestinal mucosa. Therefore, when the active ingredient is such that its efficacy is dependent on direct exposure, the duration of contact with the desired site of action is prolonged so that the pharmacological activity of the ingredient can be made fully available over a sufficient time. Moreover, even a sparingly water-soluble active ingredient can be released gradually at a selected site within the gastrointestinal tract with the result that its efficacy can be made available over a protracted time period.

In the matrix particle of matrix (A) or of matrix (B), the proportion of the viscogenic agent is about 0.005 to 95 percent by weight, preferably 0.5 to 30 percent by weight, and more preferably about 1 to 10 percent by weight, based on the total weight of the matrix composition.

The matrix (A) composition may be manufactured by dispersing the viscogenic agent, polyglycerol fatty acid ester and active ingredient and the matrix (B) composition may be prepared by dispersing the viscogenic agent, lipid and active ingredient. By way of illustration, the solid matrix containing the polyglycerol fatty acid ester or lipid and which is solid at ambient temperature is melted by heating it at a temperature above its melting point, then the viscogenic agent and the active ingredient are added and dispersed therein and the mixture is cooled to give the matrix composition. The heating temperature for the matrix may, for example, be about 40 to 150° C., preferably about 50 to 90° C.

When the active ingredient is an acidic drug, the solid base mentioned hereinbefore may be advantageously added. When it is a basic drug, the enteric polymer mentioned hereinbefore may be added. In melting the polyglycerol fatty acid ester and/or lipid, the abovementioned additive may be melted together or these materials may be respectively melted and then combined. It is also possible to add the viscogenic agent and additive in particulate form together with the active ingredient.

Fine granules or granules containing said matrix can be manufactured by means of the conventional granulating machinery. Such fine granules and granules are preferably prepared under cooling. For example, it is a preferred practice to produce spherical fine granules by spray mist cooling, particularly by spray-chilling. Spray-chilling can be effected by dropping a molten matrix at a constant flow rate on a high-speed rotating disk driven at 10 to 6,000 rpm, preferably 900 to 6,000 rpm, and more preferably 1,000 to 3,000 rpm. The rotary disk for this purpose may be a circular plate disk, smooth circular plate, made of aluminum or the like material, which has a diameter of, for example, 5 to 100 cm, preferably 10 to 20 cm. The dropping speed of the molten matrix can be selected according to the desired particle size of fine granules and is generally about 2 to 200 g/minute and preferably about 5 to 100 g/minute. The resulting granules are closer to true spheres, indicating that a more uniform coating film can be efficiently formed by using the coating composition.

The matrix (A) or (B) can also be prepared by kneading the above-mentioned components with the aid of a solvent and granulating the resultant mass. In this case, the undesirable effect of heat on the active ingredient can be avoided. Therefore, even when the active ingredient is a peptide, a protein or the like, an effective matrix composition can be easily obtained, with the deactivation of the drug being held to a minimum.

The matrix particles of the matrix (C) need only have been coated with a coating composition containing at least said viscogenic agent. The coating composition may contain, in addition to the viscogenic agent, at least one member of said polyglycerol fatty acid ester, said lipid, said enteric polymer and a water-insoluble polymer. In this case, when the viscogenic agent is a substance which is poorly compatible or incompatible with the above-mentioned components, the matrix particle thus coated has a surface film in which said viscogenic agent has been well dispersed. The coating composition may further contain said active ingredient and/or said additives.

The water-insoluble polymer mentioned hereinbefore includes, for example, hydroxypropylmethylcellulose phthalate (J.P. XI), hydroxypropylmethylcellulose acetate succinate (Shin-Etsu Chemical Co., Ltd., Japan), carboxymethylethylcellulose (Freund Industrial Co., Ltd.; CMEC, the Formulary of Non-official Drugs 1986), cellulose acetate trimellitate (Eastman Co., Ltd.), cellulose acetate phthalate (J.P. XI), ethylcellulose (Asahi Chemical Industry Co., Ltd., Japan; FMC), aminoalkyl methacrylate copolymer (Röhm Pharma; Eudragit E100, RS, RN100L, RSPML, RN100, RSPM), methacrylic acid copolymer L (Röhm Pharma, Eudragit L100), methacrylic acid copolymer L-D (Röhm Pharma, Eudragit L-30-D-55), methacrylic acid copolymer S (Röhm Pharma; Eudragit S-100), polyvinyl acetate phthalate (COLOR-CON), Eudragit NE30-D (Trade name of Röhm Pharma) and so on. These water-insoluble polymers can be used singly or in combination.

The proportion of the viscogenic agent based on the total nonvolatile matter of the coating composition is about 0.005 to 100 percent by weight, preferably about 0.05 to 95 percent by weight, more preferably about 0.5 to 30 percent by weight, and particularly about 1 to 10 percent by weight.

When the viscogenic agent is used in combination with at least one of polyglycerol fatty acid ester, lipid, enteric polymer and water-insoluble polymer, the proportion of the viscogenic agent is about 0.005 to 95 percent by weight, preferably about 0.5 to 30 percent by weight, and more preferably about 1 to 10 percent by weight based on the total nonvolatile matter of the coating composition.

In the coating composition may be incorporated two or more components selected from among said polyglycerol fatty acid ester, lipid, enteric polymer and water-insoluble polymer. When said polyglycerol fatty acid ester and/or lipid is used in combination with another component selected from among said enteric polymer and water-insoluble polymer, the preferred proportion of such other component to each part by weight of the polyglycerol fatty acid ester and/or lipid is about 0.0001 to 1,000 parts by weight, preferably about 0.01 to 100 parts by weight, and more preferably about 0.01 to 10 parts by weight.

The coating amount of the coating composition can be selected according to the type of solid preparation and the desired strength of adhesion to the mucosa. The coating amount relative to the solid preparation is about 0.1 to 30 percent by weight and preferably about 0.5 to 10 percent by weight for tablets, about 0.1 to 50 percent by weight and preferably about 1 to 20 percent by weight for pills and granules, and about 0.1 to 100 percent by weight and preferably about 1 to 50 percent by weight for fine granules.

In the coating procedure, the common additives mentioned hereinbefore may be incorporated in the coating composition or may be applied independently of the coating composition. The proportion of such additives to be added may for example be about 0.1 to 70 percent by weight, preferably about 1 to 50 percent by weight, more preferably about 20 to 50 percent by weight based on the nonvolatile matter of the coating composition.

Coating can be carried out by the conventional manner, such as pan coating, air-suspension or fluidized bed coating, centrifugal coating and so on. When the coating composition is a solution or dispersion containing water or an organic solvent, the spray-coating method can also be employed. The proportion of such water or organic solvent may for example be about 25 to 99 percent by weight. The type of organic solvent is not so critical. Thus, for example, alcohols such as methanol, ethanol, isopropyl alcohol, and the like; ketones such as acetone and the like; and halogenated hydrocarbons such as chloroform, dichloromethane, trichloroethane, and the like can be employed.

When the polyglycerol fatty acid ester and/or lipid is incorporated in the coating composition of the invention, a coated pharmaceutical product can be manufactured by melting the polyglycerol fatty acid ester and/or lipid, with or without addition of other additives, at an elevated temperature, emulsifying the molten mass with water, spraying the surface of the substrate preparation with the resulting emulsion and drying the coated preparation. An alternative method may comprise preheating the solid substrate preparation with a hot current of air in a coating pan or the like and feeding the coating composition to the pan so that it may melt and spread over the substrate preparation.

The coating of such a solid preparation is usually carried out at a temperature of 25 to 60° C. and preferably 25 to 40° C.

The coating time can be selected according to the coating method, the characteristics and amount of the coating composition and the characteristics of the substrate preparation, among other things.

Fine granules, granules, pills, tablets and other dosage forms can be rendered adherent to the mucosa by using the coating composition of the invention. The coating composition can be applied to a broad range of drug substances. For example, it can be applied not only to a matrix particle prepared by melting the polyglycerol fatty acid ester or lipid, and the like at an elevated temperature and adding an active ingredient thereto but also to a matrix particle containing a physiologically active peptide or protein which is easily deactivated by heat. A matrix particle containing such a thermolabile active ingredient can be manufactured by granulating the active ingredient and said additives, such as binder, excipient, disintegrator, and the like, together with said lipid where necessary, without using a polyglycerol fatty acid ester, at a low temperature not causing deactivation of the active ingredient. The matrix particle can also be manufactured by dispersing said components in water or an organic solvent with use of a kneader or the like and granulating the kneaded mass.

For all of the matrixes (A), (B) and (C), insofar as the viscogenic agent is allowed to exhibit its mucosal adhesivity in the gastrointestinal tract, the matrix may, where necessary, have an enteric or gastric coating or the like. For example, when the matrix has an enteric coating layer which is adapted to dissolve in the vicinity of the site of absorption, the matrix will adhere to the site of absorption to function as a target-oriented drug delivery system.

The solid preparation according to the present invention may be provided in a variety of dosage forms such as fine granules, granules, pills, tablets obtainable by compression-molding the fine granules or granules, and capsules obtainable by filling capsules with the fine granules or granules. Preferred dosage forms are fine granules and granules. The lipid-containing matrixes (A) and (C) are suitable for fine granules. The particle size distribution of the fine granules may, for example, be 10 to 500 $\mu$m for 75 weight % or more of their total weight, more than 500 $\mu$m for not more than 5 weight %, and less than 10 $\mu$m for not more than 10 weight %. The preferred particle size distribution of the fine granules is 105 to 500 $\mu$m for not less than 75 weight %, more than 500 $\mu$m for not more than 5 weight %, and not more than 74 $\mu$m for not more than 10 weight %. The particle size distribution of the granules may, for example, be 500 to 1410 $\mu$m for not less than 90 weight % and not more than 177 $\mu$m for not more than 5 weight %. The following examples and comparative example are merely intended to illustrate the present invention in further detail and should not be construed as defining the scope of the invention.

EXAMPLES

Example 1

Ten grams of stearyl penta(tetra)glyceride (Sakamoto Yakuhin Kogyo Co., Ltd. Japan; PS-310) was melted by heating at 85° C. Six grams of idebenone and 2 g of an acrylic acid polymer (The B. F. Goodrich Company; Carbopol 934P) were added to the melt, and the resultant mixture was stirred at 80° C. for 15 minutes to give a dispersion. The molten mixture was then dropped onto an aluminum disk (15 cm in diameter) rotating at 1,500 rpm at a rate of 10 g per minute, whereby spherical fine granules passing through a 30-mesh sieve but failing to pass through an 80 mesh sieve (hereinafter referred to briefly as 30/80 mesh) were obtained.

Example 2

The procedure of Example 1 was followed using 11.5 g of stearyl penta(tetra)glyceride, 6.0 g of idebenone and 0.5 g of the same acrylic acid polymer as used in Example 1 to give 30/80 mesh spherical fine granules.

Example 3

The same stearyl penta(tetra)glyceride as used in Example 1 (100 g) was melted by heating at 85° C., 60 g of idebenone was added, and the mixture was stirred for 15 minutes. The molten mixture thus obtained was dropped onto an aluminum disk (15 cm in diameter) rotating at 1,500 rpm at a rate of 10 g per minute, whereby 30/80 mesh spherical fine granules were obtained.

The same acrylic acid polymer as used in Example 1 (4 g) was dispersed in 200 ml of ethanol to give a coating solution.

A centrifugal granulator (Freund Industries, model CF) was charged with 50 g of the above fine granules. coating was conducted by adding the above coating solution at a rate of 1 ml per minute while a rotating speed of 600 rpm, a hot air temperature of 46° C. and a granule temperature of 32° C. were maintained. Coated fine granules were thus obtained.

Comparative Example 1

The procedure of Example 3 was followed using 50 g of the same stearyl penta(tetra)glyceride as used in Example 1 and 100 g of idebenone but omitting the acrylic acid polymer coating to give 30/80 mesh spherical fine granules.

Test Example 1

The fine granules obtained in Example 3 and those obtained in Comparative Example 1 were respectively administered orally to rats (weighing 450 g, 12 weeks of age) fasted for 24 hours in a dose of 100 mg/kg together with 0.2 ml of water. Three hours later, the rats were laparotomized and the interior of the stomach was examined. The fine granules obtained in Comparative Example 1 were absent in the stomach whereas the fine granules obtained in Example 3 were found adhering to the stomach wall.

Example 4

The procedure of Example 3 was followed using 100 g of the same stearyl penta(tetra)glyceride as used in Example 1, 80 g of idebenone and 20 g of corn starch to give coated fine granules.

Example 5

The procedure of Example 1 was followed using 12 g of the same stedryl penta(tetra)glyceride, 4 g of stearyl mono (tetra)glyceride (Sakamoto Yakuhin Kogyo Co., Ltd., Japan; MS-310), 2 g of riboflavine and 2 g of the same acrylic acid polymer as used in Example 1 to give 30/80 mesh spherical fine granules.

Examples 6 and 7

The procedure of Example 1 was followed using the polyglycerol fatty acid esters specified below, riboflavine and the Acrylic acid polymer specified below in the respective amounts (g) shown below to give 30/80 mesh spherical fine granules.

|  | Example 6 | Example 7 |
| --- | --- | --- |
| Stearyl penta(tetra)glyceride | 12.75 | 13.125 |
| Stearyl mono(tetra)glyceride | 4.25 | 4.375 |
| Riboflavine | 2 | 2 |
| Acrylic acid polymer (same as used in Example 1) | 1 | 0.5 |

Example 8 to 10

The procedure of Example 1 was followed using the polyglycerol fatty acid ester specified below, acetaminophen and the acrylic acid polymer specified below in the respective amounts (g) shown below to give 30/80 mesh spherical fine granules.

|  | Example 8 | Example 9 | Example 10 |
| --- | --- | --- | --- |
| Stearyl penta(tetra) glyceride | 13.5 | 13 | 12 |
| Acetaminophen | 6 | 6 | 6 |
| Acrylic acid polymer (same as used in Example 1) | 0.5 | 1 | 2 |

Example 11

The procedure of Example 1 was followed using 147.0 g of stearyl penta(tetra)glyceride, 13.4 g of stearyl mono(tetra) glyceride, 15.0 g of vinpocetine and 27.6 g of the same acrylic acid polymer as used in Example 1 to give 30/60 mesh spherical fine granules.

Example 12

The procedure of Example 1 was followed using 79.1 g of stearyl penta(tetra)glyceride, 8.4 g of stearyl mono(tetra) glyceride, 62.0 g of a methacrylic acidmethyl methacrylate copolymer [Röhm Pharma (Germany); Eudragit L100-551] and 7.5 g of vinpocetine to give 30/80 mesh spherical fine granules.

The fine granules obtained were then coated in the same manner as in Example 3 using the same coating solution as used in Example 3 to give coated fine granules.

Example 13

The procedure of Example 1 was followed using 18 g of stearyl penta(tetra)glyceride, 1 g of phenylpropanolamine hydrochloride and 1 g of an acrylic acid polymer (Wako Pure Chemical Industries; HIVISWAKO 104) to give 30/80 mesh spherical fine granules.

Example 14

The procedure of Example 1 was followed using 10 g of stearyl penta(tetra)glyceride, 8 g of AD-5467 and 2 g of the same acrylic acid polymer as used in Example 1 to give 30/80 mesh spherical fine granules.

Comparative Example 2

The procedure of Example 1 was followed using 10 g of stearyl penta(tetra)glyceride and 10 g of AD-5467 to give 30/80 mesh spherical fine granules.

Test Example 2

The fine granules obtained in Example 14 and those obtained in Comparative Example 2 were respectively administered orally to rats in the same manner as in Test Example 1. Three hours later, the rats were laparotomized and the interior of the stomach was examined. The fine granules obtained in Comparative Example 2 were absent in the stomach whereas the fine granules obtained in Example 14 were found adhering to the stomach wall.

Test Example 3

One hundred 30/40 mesh fine granules as sorted from the fine granules obtained in Example 14 and Comparative Example 2 were respectively administered orally to rats (weight 300 to 400 g, 10 to 12 weeks of age) fasted for 24 hours together with 0.5 ml of water. At 1, 3, 5 or 8 hours after administration, the rats were laparotomized and the fine granules remaining in the stomach and the upper part, middle part, and lower part of the small intestine were respectively counted and the mean values were calculated. The results are shown in Table 1.

TABLE 1

| Time elapsed (hrs) |  | Stomach | Small intestine | | |
| --- | --- | --- | --- | --- | --- |
|  |  |  | Upper | Middle | Lower part |
| 1 | Example 14 | 78.4 | 9.4 | 6.1 | 0 |
|  | Comparative Example 2 | 20.8 | 4.3 | 42.8 | 2.0 |
| 3 | Example 14 | 25.3 | 7.3 | 22.3 | 40.5 |
|  | Comparative Example 2 | 2.3 | 4.6 | 4.2 | 62.5 |
| 5 | Example 14 | 5.5 | 2.0 | 16.0 | 66.3 |
|  | Comparative Example 2 | 0.3 | 0 | 3.0 | 39.7 |
| 8 | Example 14 | 1.0 | 9.5 | 15.3 | 18.9 |
|  | Comparative Example 2 | 0 | 0 | 0.4 | 2.7 |

Example 15

The procedure of Example 1 was followed using 10 g of hardened cotton seed oil, 8 g of AD-5467 and 2 g of the same acrylic acid polymer as used in Example 13 to give 30/80 mesh spherical fine granules.

Example 16

The procedure of Example 1, was followed using 16 g of stearic acid, 2 g of riboflavine and 2 g of the same acrylic acid polymer as used in Example 13 to give 30/80 mesh spherical fine granules.

Example 17

The procedure of Example 1, was followed using 27 g of stearyl penta(tetra)glyceride, 3 g of microcrystalline wax (Nippon Seiro Co., Ltd., Japan; Hi-Mic 1080), 2 g of vinpocetine and 8 g of the same acrylic acid polymer as used in Example 13 to give 30/80 mesh spherical fine granules.

Test Example 4

A mixture of 16 g of stearyl penta(tetra)glyceride and 0.5 g of stearyl mono(tetra)glyceride was melted by heating at 85° C. Then, 4 g of a viscogenic agent selected from among the 12 substances mentioned below was added, and the resultant mixture was stirred at 80° C. for 15 minutes to effect dispersion.

Acrylic acid polymers: Carbopol 934P, HIVISWAKO 103, HIVISWAKO 104.

Cellulose ethers: HPMC-65SH50, HPMC-65SH4000 (hydroxypropylmethylcellulose 2906), TC-5 (hydroxypropylmethylcellulose 2910), CMC-sodium.

Naturally occurring viscogenic agents: Pectin, tragacanth gum, xanthan gum, gelatin, agar.

The molten mixture was dropped onto an aluminum disk (15 cm in diameter) rotating at 1,500 rm at a rate of 10 g per minute to give 30/42 mesh spherical fine granules.

In a control run, 16 g of stearyl penta(tetra)glyceride and 0.5 g of stearyl mono(tetra)glyceride were melted by heating at 85 ° C. and the molten mixture was dropped onto an aluminum disk (15 cm in diameter) rotating at 1,500 rpm at a rate of 10 g per minute to give 30/42 mesh spherical fine granules.

The fine granules obtained as described above were subjected to in vitro and in vivo tests for investigating the degree of adhesion to the mucosa by the following methods.

In vitro observation

The small intestine of rats (body weights 400 to 500 g, 12 weeks of age) was isolated and washed with several portions of physiological saline. The isolated small intestine was cut to a length of 4 cm and the resulting strip was longitudinally incised. Then, with its mucosal side up, the intestinal strip was mounted on a plastic holder and washed again with several portions of saline. The test fine granules were placed uniformly on the mucosa of the small intestine and the tissues of the small intestine with the granules were placed in a desiccator (93% RH, room temperature) for 20 minutes. Then, the strip was taken out, washed with saline using a peristaltic pump (flow rate 22 ml/min.) and observed for any adherent fine granules.

The degree of adhesion of fine granules was evaluated according to the following criteria. The results are set forth in Table 2.

TABLE 2

| Viscogenic agent | Degree of adhesion |
| --- | --- |
| Carbopol 934P | Excellent |
| HIVISWAKO 103 | Excellent |
| HIVISWAKO 104 | Excellent |
| HPMC-65SH50 | Fair |
| HPMC-65SH4000 | Fair |
| TC-5 | Fair |
| CMC-sodium | Fair |
| Pectin | Good |
| Tragacanth gum | Good |
| Xanthan gum | Fair |
| Gelatin | Fair |
| Agar | Good |
| Control (no viscogenic agent) | Poor |

Excellent: Very many adherent fine granules
Good: Many adherent fine granules
Fair: Some adherent fine granules
Poor: No adherent fine granules In the in vitro observation, the control fine granules showed no adhesion to the intestinal mucosa. In contrast, the fine granules containing viscogenic agents were found to be adherent to the intestinal mucosa. Particularly excellent adhesion was found for fine granules containing Carbopol 934P, HIVISWAKO 103 and HIVSWAKO 104, respectively.

In vivo observation

Test fine granules were administered orally to rats fasted for 24 hours (body weights 400 to 500 g, 12 weeks of age) in a dose of 100 mg/kg together with 0.5 ml of water. After 3 hours, a laparotomy was performed and the gastric mucosa was examined for adhesion of the fine granules. The degree of adhesion was evaluated according to the same criteria as above. The results are set forth in Table 3.

TABLE 3

| Viscogenic agent | Degree of adhesion |
| --- | --- |
| Carbopol 934P | Excellent |
| HIVISWAKO 103 | Excellent |
| HIVISWAKO 104 | Excellent |
| HPMC-655H50 | Good |
| HPMC-65SH4000 | Good |
| TC-5 | Fair |
| CMC-sodium | Fair |
| Pectin | Fair |
| Tragacanth gum | Fair |
| Xanthan gum | Fair |
| Gelatin | Fair |
| Agar | Good |
| Control (no viscogenic agent) | Poor |

In the in vivo observation, the control fine granules were not detected in the stomach but the fine granules containing viscogenic agents were found in the stomach. Particularly the fine granules containing Carbopol 934P, HIVISWAKO 103 and HIVISWAKO 104, respectively, were found adhering in large numbers to the gastric wall.

Example 18

The procedure of Example 1 was followed using 50 g of stearyl penta(tetra)glyceride (Sakamoto Yakuhin Kogyo Co., Ltd.; PS-310), 40 g of indomethacin and 10 g of an acrylic acid polymer (Wako Pure Chemical Industries; HIVISWAKO 104) to give 30/80 mesh spherical fine granules.

Test Example 5

The fine granules obtained in Example 18 were orally administered, in the same manner as in Test Example 1, to rats (weighing 300 g, 9 weeks of age) fasted for 24 hours at a dose of 5 mg (as indomethacin) per kg.

In a control group, the same rats as mentioned above were orally given an arabic gum suspension containing 5 % by weight of indomethacin at a dose of 5 mg (as indomethacin) per kg.

The plasma levels ($\mu$g/ml) of indomethacin were followed by blood sampling from the rat caudal vein at timed intervals. The results thus obtained are shown below in Table 4.

TABLE 4

| | Blood level ($\mu$g/ml) | | | | | | |
| --- | --- | --- | --- | --- | --- | --- | --- |
| Time (hr) | 1 | 2 | 3 | 5 | 8 | 11 | 24 |
| Example 18 | 2.5 | 6.5 | 8.9 | 10.1 | 9.2 | 9.2 | 1.1 |
| Control | 17.9 | 17.5 | 14.6 | 11.3 | 7.5 | 4.1 | 0.3 |

Example 19

The procedure of Example 1 was followed using 101.25 g of stearyl penta(tetra)glyceride (Sakamoto Yakuhin Kogyo Co., Ltd.; PS-310), 3.75 g of stearyl mono(tetra)glyceride (Sakamoto Yakuhin Kogyo Co., Ltd.; MS-310), 7.5 g of vinpocetine, 15 g of magnesium hydroxide and 22.5 g of an acrylic acid polymer (Wako Pure Chemical Industries; HIVISWAKO 104) to give 30/80 mesh spherical fine granules.

Example 20

The procedure of Comparative Example 2 was followed using 40 g of behenyl hexa(tetra)glyceride (Riken Vitamin Co., Ltd.; Poem J-46B) and 10 g of acetaminophen to give 60/100 mesh spherical fine granules.

One part by weight of the fine granules obtained were admixed with 1 part by weight of a molten mixture [stearyl penta(tetra)glyceride (Sakamoto Yakuhin Kogyo Co., Ltd.; PS-310): acrylic acid polymer (Wako Pure Chemical Industries; HIVISWAKO 104): lactose=16:3:1 (by weight)]. The resultant molten mixture was dropped onto an aluminum disk (15 cm in diameter) rotating at 1,500 rpm at a rate of 10 g per minute, whereby 30/80 mesh spherical fine granules were obtained.

Text Example 6

The fine granules obtained in Example 20 were orally administered to rats in the same manner as in Test Example 1. Three hours later, the rats were laparotomized and the interior of the stomach was examined. The fine granules were found adhering to the stomach wall.

Example 21

The procedure of Example 1 was followed except that 10 g of stearyl penta(tetra)glyceride, 8 g of chlorothiazide and 2 g of the same acrylic acid polymer as used in Example 1 were employed to give 30/80 mesh spherical fine granules.

Comparative Example 3

The procedure of Example 1 was followed except that 10.6 g of stearyl penta(tetra)glyceride, 5.4 g of stearyl mono(tetra)glyceride and 4 g of chlorothiazide were employed to give 30/80 mesh spherical fine granules.

Test Example 7

The fine granules prepared in Example 21 and Comparative Example 3 were respectively administered orally to rats and 3 hours later the animals were laporotomized and observed for the interior of the stomach as in Test Example 1. It was found that whereas the fine granules according to Comparative Example 3 were absent in the stomach, the fine granules of Example 21 remained on the gastric wall.

Test Example 8

The fine granules prepared in Example 21 were orally administered to rats (body weight 250 g, 8 weeks old), deprived of food for 24 hours, in a dose of 10 mg/rat together with 0.2 ml of water.

As a control, a suspension of chlorothiazide in distilled water containing 5 % (w/v) of arabic gum was orally administered in a dose of 10 mg (as chlorothiazide)/rat.

The blood was serially taken from the causal vein of the rat to investigate a time course of plasma chlorothiazide concentration (gg/ml). The results are set forth in Table 5.

TABLE 5

| | Blood level ($\mu$g/ml) | | | | | | |
|---|---|---|---|---|---|---|---|
| Time (hr) | 0.5 | 1 | 2 | 3 | 5 | 8 | 10 |
| Example 21 | 0.39 | 0.37 | 0.38 | 0.52 | 1.17 | 0.93 | 0.78 |
| Control | 0.63 | 0.50 | 0.71 | 0.58 | 0.42 | 0.34 | 0.21 |

The rats treated with the fine granules of Example 21 showed a higher plasma concentration of chlorothiazide over a longer time period.

Example 22

The procedure of Example 1 was followed except that 12 g of stearyl penta(tetra)glyceride, 6 g of buprenorphine hydrochloride and 2 g of the same acrylic acid polymer as used in Example 13 were employed to give 30/80 mesh spherical fine granules.

Example 23

The procedure of Example 1 was followed except that 9.5 g of stearyl penta(tetra)glyceride, 0.5 g of stearyl mono (tetra)glyceride, 2 g of sucralfate (Nippon Synthetic Chemical Industry, Japan; Sulcose) and 2 g of the same acrylic acid polymer as used in Example 13 were employed to give 30/80 mesh spherical fine granules.

Example 24

The procedure of Example 1 was followed except that 13.5 g of behenyl hexa(tetra)glyceride (Riken Vitamin Co., Ltd.; Poem J-46B), 0.5 g of stearyl mono(tetra)glyceride, 1 g of dihydrocodeine phosphate, 2 g of magnesium hydroxide and 2 g of the same acrylic acid polymer as used in Example 13 were employed to give 30/80 mesh spherical fine granules.

Example 25

The procedure of Example 1 was followed except that 13.5 g of behenyl hexa(tetra)glyceride, 0.5 g of stearyl mono(tetra)glyceride, 1 g of dihydrocodeine phosphate, 3 g of calcium carbonate and 2 g of the same acrylic acid polymer as used in Example 13 were employed to give 30/80 mesh spherical fine granules.

Example 26

The fine granules (25 g) obtained in Example 5 were coated in the following manner to give coated fine granules. A mini centrifugal fluid-bed equipment (CF Granulator, Freund Industries) was charged with 25 g of fine granules and with the rotor speed set at 550 rpm, a 5 % (w/v) solution of Eudragit L100-55 (Trade name of Röhm Pharma) in ethanol was sprayed at a rate of 0.7 ml/minute to give 24/80 mesh spherical fine granules.

Example 27

The procedure of Example 26 was followed except that 25 g of the fine granules obtained in Example 5 were spray-coated with a 5% (w/v) solution of hydroxypropylcellulose (Nippon Soda Co., Ltd., Japan; HPC-L) in ethanol to give 24/80 mesh spherical fine granules.

Example 28

The procedure of Example 1 was followed except that 10 g of stearyl penta(tetra)glyceride, 4 g of chlorothiazide and 2 g of NOVEON AA1 (Trade name of The B. F. Goodrich Company) to give 30/80 mesh spherical fine granules.

Example 29

Fifty grams of the fine granules obtained in Example 5 were mixed with 45 g of crystalline cellulose, 5 g of croscarmellose sodium (Ac-Di-Sol; Trade name of FMC Corporation) and 0.3 g of magnesium stearate and the mixture was compression-molded with a punch having a flat surface, 100 mm in diameter, at 0.5 ton/cm² to give tablets.

Example 30

The procedure of Example 1 was followed except that 15 g of behenyl hexa(tetra)glyceride, 2 g of AG 1789 and 3 g of the acrylic acid polymer used in Example 13 was employed to give 30/80 mesh spherical fine granules.

Test Example 9

The fine granules obtained in Example 30 were orally administered to rats and 3 hours later the animals were laparotomized and observed for the interior of the stomach as in Example 1. The fine granules were found adhering to the gastric wall.

Example 31

To 500 g of stearyl penta(tetra)glyceride was added 500 g of stearyl mono(tetra)glyceride and the mixture was melted by heating at 90° C. and dropped on an aluminum disk, 15 cm in diameter, revolving at 2,000 rpm at the rate of 20 g/minute to give 42/60 mesh spherical polyglycerol fatty acid ester granules.

A fluidized-bed granulator (Fuji Sangyo Co., Ltd., Japan; FD-3S) was charged with 100 g of the 42/60 mesh polyglycerol fatty acid ester, 50 g of the same acrylic acid polymer as used in Example 13 and 40 g of riboflavine and the charge was fluidized at an air temperature of 54° C. When it was confirmed that the floating acrylic acid polymer and riboflavin particles were no longer observed in the fluidized bed, the heat source was switched off. On cooling, there were obtained granules.

What is claimed is:

1. A gastrointestinal mucosa-adherent matrix which is solid at ambient temperature, which consists essentially of an agent capable of developing viscosity on contact with water, a lipid and an active ingredient each contained in a matrix particle, wherein said agent is an acrylic acid polymer or salt thereof each containing 58.0 to 63.0 percent by weight of carboxyl groups and having a molecular weight of 1,000,000 to 5,000,000, said agent is dispersed throughout the matrix particle, and the content of said agent is 1 to 10 percent by weight based on the total weight of said matrix particle.

2. A gastrointestinal mucosa-adherent matrix according to claim 1 wherein said lipid has a melting point of 40 to 120° C.

3. A gastrointestinal mucosa-adherent matrix according to claim 1 wherein said lipid is a $C_{14-22}$ saturated fatty acid or a salt thereof, a $C_{16-22}$ higher alcohol, a fatty acid glyceride ester, an oil, a wax, a hydrocarbon or a phospholipid.

4. A gastrointestinal mucosa-adherent matrix according to claim 1 wherein said active ingredient is an antiulcer agent or a therapeutic drug for gastritis.

5. A gastrointestinal mucosa-adherent matrix according to claim 1 wherein said active ingredient is a compound of the following formula (II) or a physiologically a acceptable salt thereof:

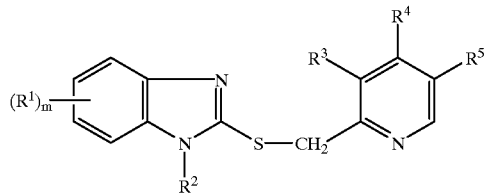

(II)

wherein $R^1$ means hydrogen, an alkyl, a halogen, cyano, carboxy, an alkoxycarbonyl, an alkoxycarbonylalkyl, carbamoyl, a carbamoylalkyl, hydroxy, an alkoxy, a hydroxyalkyl, trifluoromethyl, an acyl, carbamoyloxy, nitro, an acyloxy, an aryl, an aryloxy, an alkylthio or an alkylsufinyl; $R^2$ means hydrogen, an alkyl, acyl, an alkoxycarbonyl, carbamoyl, an alkylcarbamoyl, a dialkylcarbamoyl, an alkylcarbonylmethyl, an alkoxycarbonylmethyl or an alkylsulfonyl; $R^3$ and $R^5$ may be the same or different and each means hydrogen, an alkyl, an alkoxy or an alkoxyalkoxy; $R^4$ means hydrogen, an alkyl, an alkoxy which may be fluorinated, an alkoxyalkoxy, an alkenyloxy which may be fluorinated or an alkynyloxy which may be fluorinated and m means an integer of 0 to 4.

6. A gastrointestinal mucosa-adherent matrix according to claim 5 wherein, in said compound of the formula (II), $R^1$, $R^2$ and $R^5$ each is hydrogen and $R^3$ is hydrogen or methyl.

7. A gastrointestinal mucosa-adherent matrix according to claim 5 wherein, in said compound of the formula (II), $R^4$ is a fluorinated $C_{1-4}$ alkoxy group.

8. A gastrointestinal mucosa-adherent matrix according to claim 5 wherein, in said compound of the formula (II), $R^1$ is hydrogen, fluorine, methoxy or trifluoromethyl as substituted in position-5; $R^2$ is hydrogen; $R^3$ is hydrogen or methyl; $R^4$ is a $C_{1-4}$ alkoxy which may be fluorinated, 2-propenyloxy or allyl; $R^5$ is hydrogen or methyl; and m=1.

9. A gastrointestinal mucosa-adherent matrix according to claim 1 which comprises a water-insoluble or sparingly water-soluble solid base together with an acidic active ingredient.

10. A gastrointestinal mucosa-adherent matrix according to claim 1 which comprises an enteric polymer together with a basic active ingredient.

11. A gastrointestinal mucosa-adherent matrix according to claim 1 wherein the content of said lipid in said matrix particle is 0.001 to 10,000 parts by weight relative to one part by weight of said active ingredient.

12. A gastrointestinal mucosa-adherent matrix according to claim 1 wherein, in the matrix particle containing said lipid, said active ingredient and said agent, the content of said lipid is 0.001 to 10,000 parts by weight relative to one part by weight of said active ingredient.

13. A gastrointestinal mucosa-adherent matrix according to claim 1 wherein said matrix has a melting point of 30 to 120° C.

14. A solid pharmaceutical preparation comprising a gastrointestinal mucosa-adherent matrix particle which is solid at ambient temperature, which comprises a viscogenic agent capable of developing viscosity on contact with water and selected from the group consisting of (1) an acrylic acid polymer obtained by polymerization of a monomer containing acrylic acid as a monomer component, having a molecular weight of 1,000,000 to 5,000,000, and (2) a salt of said polymer, as dispersed at least in the neighborhood of the surface layer of the matrix particle containing a lipid and an active ingredient, wherein the content of said viscogenic agent is 1 to 10 percent by weight based on the total weight of said matrix particle.

15. A solid pharmaceutical preparation according to claim 14 which is in a dosage form selected from the group consisting of fine granules, granules, pills, tablets obtainable by compression-molding said fine granules or granules, and capsules obtainable by filling said fine granules or granules in capsules.

16. A gastrointestinal mucosa-adherent matrix particle having a melting point of 30 to 120° C., which consists essentially of (i) a lipid, (ii) an active ingredient and (iii) an agent having the property of becoming viscous on contact with water and selected from the group consisting of (1) an acrylic acid polymer obtained by polymerization of a monomer containing acrylic acid as a monomer component, having a molecular weight of 1,000,000 to 5,000,000, and (2) a salt of said polymer, the active ingredient (ii) and the agent (iii) being dispersed throughout the matrix particle, wherein the content of said agent (iii) is 1 to 10 percent by weight based on the total weight of said matrix particle.

17. A gastrointestinal mucosa-adherent matrix particle according to claim 16 wherein said active ingredient (ii) is an antiulcer agent or a therapeutic drug for gastritis.

18. A gastrointestinal mucosa-adherent matrix particle according to claim 16 wherein said active ingredient (ii) is a compound of the following formula (II) or a physiologically acceptable salt thereof:

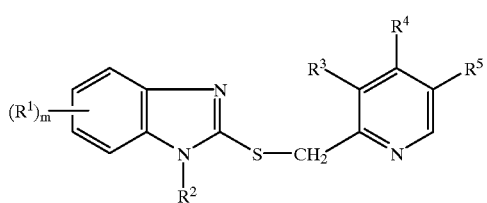

(II)

wherein $R^1$ means hydrogen, an alkyl, a halogen, cyano, carboxy, an alkoxycarbonyl, an alkoxycarbonylalkyl, carbamoyl, a carbamoylalkyl, hydroxy, an alkoxy, a hydroxyalkyl, trifluoromethyl, an acyl, carbamoyloxy, nitro, an acyloxy, an aryl, an aryloxy, an alkylthio or an alkylsufinyl; $R^5$ means hydrogen, an alkyl, acyl, an alkoxycarbonyl, carbamoyl, an alkylcarbamoyl, a dialkylcarbamoyl, an alkylcarbonylmethyl, an alkoxycarbonylmethyl or an alkylsulfonyl; $R^3$ and $R^5$ may be the same or different and each means hydrogen, an alkyl, an alkoxy or an alkoxyalkoxy; $R^4$ means hydrogen, an alkyl, an alkoxy which may be fluorinated, an alkoxyalkoxy, an alkenyloxy which may be fluorinated or an alkynyloxy which may be fluorinated; and m means an integer of 0 to 4.

19. A gastrointestinal mucosa-adherent matrix particle according to claim 18 wherein, in said compound of the formula (II), $R^1$, $R^2$ and $R^5$ each is hydrogen and $R^3$ is hydrogen or methyl.

20. A gastrointestinal mucosa-adherent matrix particle according to claim 18 wherein, in said compound of the formula (II), $R^4$ is a fluorinated $C_{1-4}$ alkoxy group.

21. A gastrointestinal mucosa-adherent matrix particle according to claim 18 wherein, in said compound of the formula (II), $R^1$ is hydrogen, fluorine, methoxy or trifluoromethyl substituted in position-5; $R^2$ is hydrogen; $R^3$ is hydrogen or methyl; $R^4$ is a $C_{1-4}$ alkoxy which may be fluorinated, 2-propenyloxy or allyl; $R^5$ is hydrogen or methyl; and m=1.

22. A gastrointestinal mucosa-adherent matrix particle according to claim 16 which comprises a water-insoluble or sparingly water-soluble solid base together with an acidic active ingredient as said active ingredient (ii).

23. A gastrointestinal mucosa-adherent matrix particle according to claim 16 which comprises an enteric polymer together with a basic active ingredient as said active ingredient (ii).

24. A gastrointestinal mucosa-adherent matrix particle according to claim 16 wherein the content of said lipid (i) in said matrix particle is 0.001 to 10,000 parts by weight relative to one part by weight of said active ingredient (ii).

25. A gastrointestinal mucosa-adherent matrix particle according to claim 16 wherein the matrix particle contains said lipid (i), the content of said lipid (i) being 0.001 to 10,000 parts by weight relative to one part by weight of said active ingredient (ii) and said agent (iii) being an acrylic acid polymer and/or a salt thereof as defined in claim 16.

26. A solid pharmaceutical preparation comprising a gastrointestinal mucosa-adherent matrix particle as defined in claim 16 having a melting point of 30 to 120° C., which particle consists essentially of (i) a lipid, (ii) an active ingredient and (iii) an agent having the property of becoming viscous on contact with water and selected from the group consisting of acrylic acid polymers and salts thereof having a molecular weight of 1,000,000 to 5,000,000, the agent (iii) being dispersed throughout the matrix-particle.

27. A solid pharmaceutical preparation according to claim 26 which is a fine granule, a granule, a pill, a tablet obtained by compression-molding said fine granules or granules, or a capsule obtained by filling said fine granules or granules in capsules.

28. A method of improving a gastrointestinal mucosa-adherent property by using a combination of (i) a lipid and (iii) an agent having the property of becoming viscous on contact with water, which comprises preparing a gastrointestinal mucosa-adherent matrix particle having a melting point of 30 to 120° C. for a solid pharmaceutical preparation, wherein the matrix particle consists essentially of (ii) an active ingredient together with the lipid (i) and the agent (iii) selected from the group consisting of (1) an acrylic acid polymer obtained by polymerization of a monomer containing acrylic acid as a monomer component, having a molecular weight of 1,000,000 to 5,000,000, and (2) a salt of said polymer, and the active ingredient (ii) and the agent (iii) are dispersed throughout the matrix particle, wherein the content of said agent (iii) is 1 to 10 percent by weight based on the total weight of said matrix particle, and administering the preparation orally.

29. A method for prolonging the residence time of (ii) an active ingredient in the gastrointestinal tract, which comprises administering a therapeutically effective amount of the active ingredient as a solid pharmaceutical preparation comprising a gastrointestinal mucosa-adherent matrix particle having a melting point of 30 to 120° C., which matrix particle consists essentially of (i) a lipid, (ii) the active ingredient, and (iii) an agent having the property of becoming viscous on contact with water and selected from the group consisting of (1) an acrylic acid polymer obtained by polymerization of a monomer containing acrylic acid as a monomer component, having a molecular weight of 1,000,000 to 5,000,000, and (2) a salt of said polymer, the active ingredient (ii) and the agent (iii) being dispersed throughout the matrix particle, wherein the content of said agent (iii) is 1 to 10 percent by weight based on the total weight of said matrix particle.

30. A method of improving a gastrointestinal mucosa-adherent property by using (iii) an agent having the property of becoming viscous on contact with water, which comprises preparing a gastrointestinal mucosa-adherent agent for a gastrointestinal mucosa-adherent matrix particle having a melting point of 30 to 120° C. for a solid pharmaceutical preparation, wherein the matrix particle consists essentially of (i) a lipid, (ii) an active ingredient, and (iii) the agent selected from the group consisting of (1) an acrylic acid polymer obtained by polymerization of a monomer containing acrylic acid as a monomer component, having a molecular weight of 1,000,000 to 5,000,000, and (2) a salt of said polymer, and the active ingredient (ii) and the agent (iii) are dispersed throughout the matrix particle, wherein the content of said agent (iii) is 1 to 10 percent by weight based on the total weight of said matrix particle, and administering the preparation orally.

31. A method for manufacturing a gastrointestinal mucosa-adherent matrix particle having a melting point of 30 to 120° C. for a solid pharmaceutical preparation, wherein the matrix particle comprises (i) a lipid and (iii) an agent having the property of becoming viscous on contact with water and selected from the group consisting of (1) an acrylic acid polymer obtained by polymerization of a monomer containing acrylic acid as a monomer component, having a molecular weight of 1,000,000 to 5,000,000, and (2) a salt of said polymer, which method comprises dispersing an active ingredient (ii) and the agent (iii) in the lipid (i) to obtain the matrix particle consisting essentially of the lipid (i), an active ingredient (ii) and the agent (iii), wherein the content of said agent (iii) is 1 to 10 percent by weight based on the total weight of said matrix particle.

32. A method for manufacturing a gastrointestinal mucosa-adherent matrix particle having a melting point of 30 to 120° C., which matrix particle comprises (i) a lipid, (ii) an active ingredient, and (iii) an agent having the property of becoming viscous on contact with water and selected from the group consisting of (1) an acrylic acid polymer obtained by polymerization of a monomer containing acrylic acid as a monomer component, having a molecular weight of 1,000,000 to 5,000,000, and (2) a salt of said polymer, the active ingredient (ii) and the agent (iii) being dispersed throughout the matrix particle, wherein the content of said agent (iii) is 1 to 10 percent by weight based on the total weight of said matrix particle, which method comprises:

(A) dispersing (ii) the active ingredient and (iii) the agent in (i) the lipid, or (B) kneading the components (i), (ii) and (iii), and granulating the resulting mass.

33. A method for manufacturing a solid pharmaceutical preparation comprising a gastrointestinal mucosa-adherent matrix having a melting point of 30 to 120° C., which matrix comprises (i) a lipid, (ii) an active ingredient, and (iii) an agent having the property of becoming viscous on contact with water and selected from the group consisting of (1) an acrylic acid polymer obtained by polymerization of a monomer containing acrylic acid as a monomer component, having a molecular weight of 1,000,000 to 5,000,000, and (2) a salt of said polymer, the active ingredient (ii) and the agent (iii) being dispersed throughout the matrix, wherein the content of said agent (iii) is 1 to 10 percent by weight based on the total weight of said matrix particle, which method comprises:

granulating the matrix to obtain uncoated granules, and optionally followed by compression-molding the uncoated granules to obtain tablets, or by filling capsules with the uncoated granules.

* * * * *